United States Patent [19]

Leevy et al.

[11] Patent Number: 4,675,284

[45] Date of Patent: Jun. 23, 1987

[54] PROCESS AND APPARATUS FOR EVALUATING LIVER DISEASE

[76] Inventors: Carroll M. Leevy, 35 Robert Dr., Short Hills, N.J. 07078; Gloria McNeil, 45 W. 105th St., New York, N.Y. 10025; Saad Habba, 2 Cain Cir., Watchung, N.J. 07060

[21] Appl. No.: 643,294

[22] Filed: Aug. 22, 1984

[51] Int. Cl.$^4$ .................. C12Q 1/68; A61K 43/00; A01N 1/02; G01N 33/48

[52] U.S. Cl. .................................. 435/6; 424/1.1; 424/3; 128/749; 128/752; 435/283; 935/77; 436/63

[58] Field of Search ............... 424/1.1, 3; 435/6, 68, 435/283; 128/749, 752; 935/77

[56] References Cited

PUBLICATIONS

Hensgens et al., Biochem. J., 170 (1978) 699–707.
Masahiro et al., Chem. Abstracts, 97(1982) #106299y.
Wijayasinghe et al., Chem. Abstracts, 100(1984) #100522y.
Chen et al., The Journal of Laboratory and Clinical Medicine, vol. 85, No. 1, pp. 103–112, Jan. 1975.
Leevy et al., Medica 3Medalc, Jun. 3, 1985, pp. 1–30.
Chen et al., Medical Clinics of North America, vol. 63, No. 3, May 1979, pp. 583–592.
Kakumu et al., Gastroenterology 72:594–595, 1977.
Leevy, The Journal of Laboratory and Clinical Medicine, vol. 61, No. 5, pp. 761–779, May 1963.
Leevy, Medicine, vol. 45, No. 6, pp. 423–433.

*Primary Examiner*—Christine M. Nucker
*Attorney, Agent, or Firm*—Weiser & Stapler

[57] ABSTRACT

There is disclosed an improved process and apparatus for treating liver biopsies wherein tritiated proline and tritiated thymidine are forced through respective liver biopsies, and thereafter the respective liver biopsies are evaluated for collagen synthesis and DNA synthesis, respectively, utilizing autoradiographic techniques.

5 Claims, 1 Drawing Figure

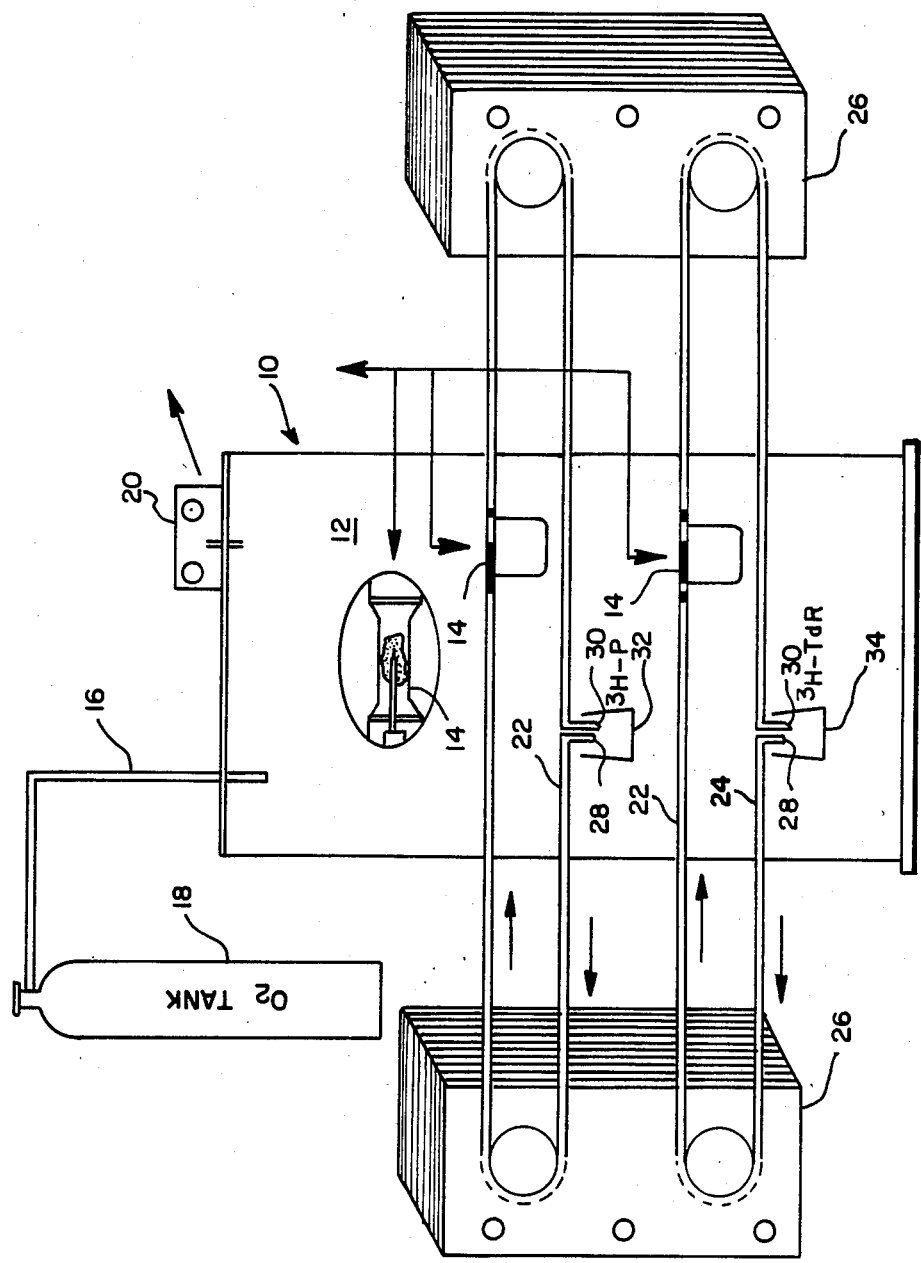

PROCESS AND APPARATUS FOR EVALUATING LIVER DISEASE

FIELD OF THE INVENTION

This invention relates to an improved process and apparatus for evaluating liver disase, and more particularly to the simultaneous assessment of kinetics of hepatic DNA and collagen synthesis.

BACKGROUND OF THE INVENTION

Liver disease is increasing in incidence, morbidity and mortality because of lack of effective preventative measures and absence of specific treatment. Therapy is largely symptomatic or supportive for fatty liver, hepatitis, cirrhosis, hepatocellular cancer and metabolic disorders which are the common diseases of the liver. The development and monitoring of the effectiveness of specific measures requires objective indices to the repair process—cell replication and fibrosis.

Incubating liver biopsies in Engles' Medium tritiated thymidine at controlled temperature, pH, and oxygen content provide objective evidence of DNA synthesis. Cells incorporating H3T into DNA were evaluated by autoradiographs and counted. It was found that (a) regenerative phases of liver injury account for progressive liver failure in chronic disease, (b) increased DNA can be recognized as the first phase of neoplasia, and (c) correction of folic acid, vitamin $B_6$, zinc and protein deficiency stimulate DNA synthesis and leads to recovery.

A similar set of circumstances was found when tritiated proline incorporation into collagen was studied. These investigations showed that liver injury, by ethanol and other noxious substances, bile duct proliferation and a fibrogenic lymphokine stimulate collagen synthesis. With elimination of the etiologic factor, early phase fibrosis due to biliary obstruction or alcoholism often disappears.

A protocol for the evaluation of nucleic acid and collagen synthesis capacity of percutaneous liver biopsies is disclosed in Medical Clinics of North America (Volume 63, No.3, May 1979). Such protocol suffered, however, from inadequay of incubation between the biopsies and the tritiated thymidine and tritiated proline as a result of inherent structure of the liver and concomitant liver biopsies, and thus did not provide quantitative results of DNA and collagen synthesis as well as any knowledge of interrelationship between such syntheses.

OBJECTS OF THE INVENTION

An object of the present invention is to provide an improved process and apparatus for assessing the kinetics of hepatic DNA and collagen synthesis in liver biopsies.

Yet another object of the present invention is to provide an improved process and apparatus for quantitatively assessing the kinetics of hepatic DNA and collagen synthesis in liver biopsies.

Still another object of the present invention is to provide an improved process and apparatus for the simultaneous assessent of hepatic DNA and collagen synthesis in percutaneous liver biopsies.

SUMMMARY OF THE INVENTION

These and other objects of the present invention are achieved by an improved process and apparatus for treating liver biopsies wherein tritiated proline and tritiated thymidine are forced through respective liver biopsies, and thereafter the respective liver biopsies are evaluated for collagen synthesis and DNA synthesis, respectively, utilizing autoradiographic techniques.

A better understanding of the present invention as well as other objects and advantages thereof will become apparent upon consideration of the detailed disclosure thereof, especially when taken with the accompanying drawing which is a schematic drawing of the process and apparatus of the present invention.

DETAILED DESCRIPTION OF THE INVENTION

Referring now to the drawing, there is provided a vessel, generally indicated as 10, defining a chamber 12 for positioning a plurality of capillary pipettes 14. The vessel 10 is provided with an inlet 16 in fluid communication with an oxygen tank 18, and with an oxygen and pressure gauge 20. The capillary pipettes 14 are in communication with conduits 22 and 24 of peristaltic pumps 26. The conduits 22 and 24 including inlet and outlet orifices 28 and 30, respectively, are disposed in reagant vessels 32 and 34, respectively.

In operation, percutaneous liver biopsies, e.g. 5 mm. pieces are disposed in pipettes 14 filled with enriched plasma, and the conduits 22 and 24 are connected thereto. Tritiated proline and tritiated thymidine at an appropriate pH are introduced into vessels 32 and 34, respectively. Oxygen from the tank 18 is introduced via conduit 16 and under the control of meter and pressure gauge 20, the chamber 12 is placed under an oxygen atmosphere and the temperature therein maintained at about 37° C. The peristaltic pumps 26 are activated to effect fluid flow through the conduits 22 and 24 of tritiated proline and tritiated thymidine coursed under pressure through the respective biopsies with a perfusate collected under vacuum of the peristaltic pumps 26.

After a predetermined time period the biopsies are fixed, e.g. by formalin, removed from the pipettes, dipped into an emulsion, e.g. Kodak NTB III and autoradiograph developed for scanning using electron microscopy as known to one skilled in the art.

DNA syntheses is expressed as the number of labelled cells per 10,000 hepatocytes and collagen synthesis graded from 1+ (minimal labelling) to 4+ (extensive labelling).

The results of the process and apparatus of the present invention is described in the following examples which are intended to be merely illustrative, and the present invention is intended not to be limited thereto.

EXAMPLES

Adult male Sprague Dawley rats (30) were given 0.5 ml of $CCl_4$ orally as a single dose or 3 times weekly for 5 months and in vitro and in vivo labelling patterns were observed to be identical. A significant increment in collagen synthesis preceded an increase in DNA synthesis in acute injury and was the dominant morphologic feature after prolonged administration of $CCl_4$. Similar results were obtained in 16 patients with active liver disease.

The process of the present invention furnished information on the relationship of hepatic regeneration and fibrogenesis and permitted monitoring of the effects of various forms of therapy on these parameters including use of nucleogenic vitamins and receipt of androgenic anabolic steroids.

While the invention has been described in connection with an exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed:

1. In a process for assaying a liver biopsy with a tritiated reagent which comprises
   contacting the liver bipsy with a tritiated reagent and
   evaluating the liver biopsy cells which have incorporated the tritiated reagent by autoradiographs,
   the improvement wherein the tritiated reagent is perfused under pressure through the liver biopsy.
2. The process of claim 1 wherein the tritiated reagent is tritiated proline.
3. The process of claim 1 wherein the tritiated reagent is tritiated thymidine.
4. The process of claim 1 which further comprises collecting the tritiated reagent perfusate under vacuum.
5. The process of claim 4 wherein the vacuum is generated by a pump.

* * * * *